US005516677A

United States Patent [19]
Kilbane, II

[11] Patent Number: 5,516,677
[45] Date of Patent: * May 14, 1996

[54] **ENZYME FROM *RHODOCOCCUS RHODOCHROUS* ATCC 53968, *BACILLUS SPHAERICUS* ATCC 53969 OR A MUTANT THEREOF FOR CLEAVAGE OF ORGANIC C—S BONDS**

[75] Inventor: John J. Kilbane, II, Woodstock, Ill.

[73] Assignee: Institute of Gas Technology, Des Plaines, Ill.

[ * ] Notice: The portion of the term of this patent subsequent to Mar. 26, 2008, has been disclaimed.

[21] Appl. No.: 270,456

[22] Filed: Jul. 5, 1994

Related U.S. Application Data

[60] Division of Ser. No. 890,190, May 28, 1992, Pat. No. 5,344,778, which is a continuation-in-part of Ser. No. 486,597, Feb. 28, 1990, Pat. No. 5,132,219.

[51] Int. Cl.$^6$ .............................. C12N 9/14; C12N 1/12; C12P 11/00; C10G 32/00
[52] U.S. Cl. ................. 435/195; 435/41; 435/130; 435/262.5; 435/282; 435/252.5; 435/252.1; 435/832; 435/822
[58] Field of Search .................................. 435/183, 195, 435/41, 130, 262.5, 282, 252.5, 252.1, 832, 822

[56] References Cited

U.S. PATENT DOCUMENTS

| | | | |
|---|---|---|---|
| 2,641,564 | 6/1953 | Zobell | 435/282 |
| 2,975,103 | 3/1961 | Kirshenbaum | 435/282 |
| 4,055,468 | 10/1977 | Umezawa et al. | 435/68.1 |
| 4,206,288 | 6/1980 | Detz et al. | 435/267 |
| 4,562,156 | 12/1985 | Isbister et al. | 435/253.3 |
| 4,632,906 | 12/1986 | Kopacz | 435/282 |
| 4,659,670 | 4/1987 | Stevens, Jr. et al. | 435/262 |
| 5,002,888 | 3/1991 | Kilbane, II | 435/252.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,232,854 | 8/1993 | Monticello | 435/282 |

FOREIGN PATENT DOCUMENTS 50-107002 8/1975 Japan.

OTHER PUBLICATIONS

Eligwe, C. A., "Microbial Desulfurization of Coal," Fuel, 67:451–458 (1988).

Ngaiza, O. G., Wise, D. L., and Gilbert, I. R., "Enzymatic Removal of Organic Sulfur from Coal," Amer. Chem. Soc. Div. Fuel Chem., 33(4) pp. 623–630, (1988).

Hartdegen, F. J., Coburn, J. M., and Roberts, R. L., "Microbial Desulfurization of Petroleum," Chem. Eng. Progress, vol. 80, No. 5 pp. 63–67 (1984).

Eckart, V., Hieke, W., Bauch, J., and Gentzsch, H., "Microbial Desulfurization of Petroleum and Heavy Petroleum Fractions. 1. Studies on Microbial Aerobic Desulfurization of Romashkino Crude Oil," Zentralbl. Microbiol. 135(8), 674–681 (1980), Chemical Abstracts, vol. 94, No. 142230q, (1981).

Eckart, V., Hieke, W., Bauch, J., and Gentzsch, H., "Microbial Desulfurization of Petroleum and Heavy Petroleum Fractions. 3. Change in the Chemical Composition of Fuel–D–Oil by Microbial Aerobic Desulfurization," Zentralbl. Microbial. 137(4), 270–279 (1982), Chemical Abstracts, vol. 97, No. 147259c, (1982).

Lee, Min Jai and Oh, Myung Soo, "Isolation, Identification, and Physiological Characteristics of Some Sulfur–Reducing Microbes," Misaengmul Hakhoe Chi, 10(4), 175–190, (1972) Chemical Abstracts, vol. 78, No. 94605m (1973).

Bauch, J., Gentzsch, H., Hieke, W., Echart, V., Koehler, M., and Babenzin, H. D., "Oxidative Microbiological Desulfurization of Heavy Petroleum Fractions," DD Patent 108,533, 20 Sep. (1974), Chemical Abstracts, vol. 83, No. 82530y (1975).

Yuda, Sadayuki, "Petroleum Desulfurization by *Pseudomonas haconensis*," Japanese Patent 75.107,002, 23 Aug. (1975) Chemical Abstracts, vol. 84, No. 46982j (1976).

Lee, M. J., Hah, Y. C., and Lee, K. W., "Desulfurization of Petroleum by Microorganisms. I. Isolation and Identification of Sulfur–Oxidizing and Reducing Bacteria," Haksurwon Nonmunjip, Chi'yon Kwahak P'yon 12, 21–49, (1973), Chemical Abstracts, vol. 85, No. 156414d (1976).

Lee, M. J., Hah, Y. C. and Lee, K. W., "Desulfurization of Petroleum by Microorganisms. III. Desulfurization of Petroleum by Contact Reaction with Desulfurizing Bacteria," Haksurwon Nonmunjip, Cha'yon Kwahak P'yon 12, 73–95, (1973). Chemical Abstracts, vol. 85, No. 145448s (1976).

Malik, K. A., "Microbial Removal of Organic Sulfur from Crude Oil and the Environment. Some New Perspectives," Process Biochem., 13(9), 10–13 (1978).

Knecht, A. T., Jr., Thesis Dissertation, Louisiana State University, Order No. 621235 (1961).

Laborde, A. L., and Gibson, D. T., "Metabolism of Dibenzothiophene by a Beijerinckia Species," Appl. Environ Microbial., 34, 783–790 (1977).

Hou, C. T. and Laskin, A. I., "Microbial Conversion of Dibenzothiophene," Dev. Ind. Microbial., 17, 351–362 (1976).

(List continued on next page.)

Primary Examiner—David M. Naff
Assistant Examiner—Michael V. Meller
Attorney, Agent, or Firm—Speckman, Pauley & Fejer

[57] ABSTRACT

A process for organic C—S bond cleavage of a sulfur-containing organic carbonaceous material by contacting the carbonacous material with a sulfur specific reactant of membrane fragments, an enzyme, or a composition of enzymes having the ability to selectively react with sulfur by cleavage of organic C—S bonds. Preferred are sulfur specific reactants associated with cell membranes of *Rhodococcus rhodochrous* strain ATCC No. 53968 and *Bacillus sphaericus* strain ATCC No. 53969 and their derivatives which have the ability to selectively react with organic sulfur of sulfur-containing organic carbonaceous material by cleavage of organic C—S bonds.

3 Claims, No Drawings

OTHER PUBLICATIONS

Isbister, J. D. and Kobylinski, E. A., "Microbial Desulfurization of Coal in Processing and Utilization of High Sulfur Coals," Coal Science and Technology Series, No. 9, 627, Attia Y. A., Ed. Amsterdam: Elsevier (1985).

Kodama, K., Nakatini, S., Umehara, K., Shimizu, K., Minoda, Y., and Yamada, K., "Microbial Conversion of Petrosulfur Compounds: Isolation and Identification of Products from Dibenzothiophene," Agr. Biolog. Chem., 34, 1320–1324 (1970).

Monticello, D. J., Bakker, D., and Finnerty, W. R., "Plasmid Mediated Degradation of Dibenzothiophene by Pseudomonas Species," Appl. Environ. Microbial., 49, 756–760 (1985).

Kargi, F. and Robinson, J. M., "Microbial Oxidation of Dibenzothiophene by the Thermophilic Organisms *Sulfolobus acidocaldarius*," Biotech. and Bioeng., 126, 687–690 (1984).

van Afferden, M., Schacht, S., Klein, J. and Trupper, H. G., "Degradation of Dibenzothiophene by Brevibacterium sp.DO", Arch. of Microbiol., 153, 324–328 (1990).

Kilbane, John J., "Sulfur–Specific Microbial Metabolism of Organic Compounds," Bioprocessing of Coals Workshop, Tysons Corner, Virginia, Aug. 16–18, 1988.

Omori, T., Monna, L., Saiki, Y., and Kodama, T., "Desulfurization of Dibenzothiophene by Corynebacterium sp. Strain SY1" App. & Environ. Microbiol. 58, 3, 911–915, Mar. (1992).

Martinek, K., Levashov, A. V., Klyachko, N., Khmelnitski, Y. L., and Berezin, I. V., "Micellar Enzymology", *J. Biochem.*, 155, 453–468 (1986).

Khmelnitsky, Y. L., Levashov, A. V., Klyachko, N. L., and Martinek, K., "Engineering Biocatalytic Systems in Organic Media with Low Water Content", *Enzyme Micro. Technol.*, 10 (Dec., 1988).

Lee, K. I. and Yen, T. F., "Coal Desulfurization Through Reverse Micelle Biocatalysis Process," ACS Div. of Fuel Chemistry, Int'l. Symposium, Los Angeles, Sep. 25–30.

MacMichael et al. *Applied and Environmental Micrology*, vol. 53, No. 1, Jan. 1977, pp. 65–69.

ENZYME FROM *RHODOCOCCUS RHODOCHROUS* ATCC 53968, *BACILLUS SPHAERICUS* ATCC 53969 OR A MUTANT THEREOF FOR CLEAVAGE OF ORGANIC C—S BONDS

CROSS REFERENCE TO RELATED APPLICATION

This is a divisional application of U.S. patent application Ser. No. 07/890,190, filed 28 May 1992, now U.S. Pat. No. 5,344,778, which application is a continuation-in-part of U.S. patent application Ser. No. 07/486,597, filed 28 Feb. 1990, now U.S. Pat. No. 5,132,219.

BACKGROUND OF THE INVENTION

FIELD OF THE INVENTION

This invention relates to selective removal of organically bound sulfur from carbonaceous materials while maintaining the calorific value of the carbonaceous materials. Useful in the process of this invention are membrane fragnents and enzymes from membrane fragments extracted from microorganisms, the membrane fragments and enzymes having the ability of selective cleavage of organic C—S bonds, such as from microorganisms *Rhodococcus rhodochrous* and *Bacillus sphaericus* and their derivatives. Particularly preferred are bacterial produced membrane extracts and enzymes of *Rhodococcus rhodochrous* ATCC No. 53968 and *Bacillus sphaericus ATCC No.* 53969. The process of this invention is particularly useful in removal of organic sulfur from fossil fuels, such as sulfur-containing coal and oils.

DESCRIPTION OF RELATED ART

Sulfur content of carbonaceous fuels, such as coals and oils, has prevented utilization of a considerable amount of such materials due to deleterious effect upon the environment. Inorganic pyritic sulfur and organically bound sulfur may each constitute as much as about 3.5 weight percent or more of coal. Pyritic sulfur has been found to be relatively easy to remove by techniques including heavy media separation, selective agglomeration, flotation, jigging, magnetic separation, leaching and hydrosulfurization. Microbial metabolism of inorganic pyritic sulfur by its oxidation using bacteria such as Thiobacillus and Sulfolobus species is known. Eligwe, C. A., "Microbial Desulfurization of Coal," *Fuel* 67:451–458 (1988). These chemolithotropic organisms can utilize inorganic pyritic sulfur compounds as energy sources and are capable of removing 90% or more of the inorganic pyritic sulfur from coal within a few days. *Thiobacillus ferrooxidans* is taught by U.S. Pat. No. 4,206,288 as suitable for removal of pyritic sulfur from coal.

*Bacillus sulfasportare* ATCC 39909 has been taught by U.S. Pat. No. 4,632,906 to be capable of sulfur removal from coal, without differentiation between pyritic and organic sulfur. An unidentified mixed culture of seven gram negative rods (ATCC 39327) prepared by growth in situ enriched with sulfur compounds and subsequently grown in the presence of coal has been shown to reduce the sulfur content of coal by about 20 percent per day with a substantial portion being reduction of organic sulfur as taught by U.S. Pat. No. 4,659,670.

The feasibility of theoretical concepts of enzymatic removal of organic sulfur from coal has been suggested by Ngaiza, O. G., Wise, D. L., and Gilbert, I. R., "Enzymatic Removal of Organic Sulfur from Coal," *Amer. Chem. Soc. Div. Fuel Chem.*, 33(4) pages 623–630, (1988).

Removal of sulfur from petroleum hydrocarbons by contact with hydrogen in the presence of hydrogenase-producing microorganisms *Desulfovibrio desulfuricans* and Sporovibrio followed by removal of sulfur in the form of gaseous products is taught by U.S. Pat. No. 2,641,564. Removal of sulfur from petroleum by Pseudomonas is taught by Hartdegen, F. J., Coburn, J. M., and Roberts, R. L., "Microbial Desulfurization of Petroleum," Chem. Eng. Progress, Vol. 80, No. 5, pp. 63–67 (1984) to be by C—C cleavage. General teachings of various Pseudomonas for removal of sulfur from petroleum are in Eckart, V., Hieke, W., Bauch., J., and Gentzsch, H., "Microbial Desulfurization of Petroleum and Heavy Petroleum Fractions. 1. Studies on Microbial Aerobic Desulfurization of Romashkino Crude Oil," Zentralbl. Microbiol. 135(8), 674–681 (1980), Chemical Abstracts, Vol. 94, No. 142230q, (1981); Eckart, V., Hieke, W., Bauch, J., and Gentzsch, H., "Microbial Desulfurization of Petroleum and Heavy Petroleum Fractions. 3. Change in the Chemical Composition of Fuel-D-Oil by Microbial Aerobic Desulfurization," Zentralbl. Microbiol. 137(4), 270–279 (1982), Chemical Abstracts, Vol. 97, No. 147259c, (1982); Lee, Min Jai and Oh, Myung Soo, "Isolation Identification, and Physiological Characteristics of Some Sulfur-Reducing Microbes," Misaengmul Hakhoe Chi, 10(4), 175–190, (1972), Chemical Abstracts, Vol. 78, No. 94605m (1973); Bauch, J., Gentzsch, H., Hieke, W., Eckart, V., Koehler, M., and Babenzin, H. D., "Oxidative Microbiological Desulfurization of Heavy Petroleum Fractions," DD Patent 108,533, 20 Sep. (1974), Chemical Abstracts, Vol. 83, No. 82530y (1975); and Yuda, Sadayuki, "Petroleum Desulfurization by *Pseudomonas haconensis*," Japanese Patent 75.107,002, 23 Aug. (1975), Chemical Abstracts, Vol. 84, No. 46982j (1976). *Thiobacillus thiooxidans* has been identified as the most effective S-oxidizer and *Pseudomonas putrefaciens* and *Desulfovibrio desulfuricans* the most effective S-reducers in microbial removal of sulfur from petroleum, Lee, M. J., Hah, Y. C., and Lee, K. W., "Desulfurization of Petroleum by Microorganisms. I. Isolation and Identification of Sulfur-Oxidizing and -Reducing Bacteria," Haksurwon Nonmunjip, Cha'yon Kwahak P'yon 12, 21–49, (1973), Chemical Abstracts, Vol. 85, No. 156414d (1976); Lee, M. J., Hah, Y. C., and Lee, K. W., "Desulfurization of Petroleum by Microorganisms. III. Desulfurization of Petroleum by Contact Reaction with Desulfurizing Bacteria," Haksurwon Nonmunjip, Cha'yon Kwahak P'yon 12, 73–95, (1973), Chemical Abstracts, Vol. 85, No. 145448s (1976).

Organic sulfur which is chemically bound within the carbonaceous molecule can be removed either by chemical or biological means. Dibenzothiophene (DBT) is the organo-sulfur compound most persons consider representative of the form in which organic sulfur exists in naturally occurring organic carbonaceous fuels such as coal and oil and is the compound upon which the microbial metabolism of organosulfur compounds has focused. Study of DBT metabolism has been pursued by several researchers who have isolated organisms capable of metabolizing DBT including Acinetobacter, Malik, K. A., "Microbial Removal of Organic Sulfur from Crude Oil and the Environment: Some New Perspectives," Process Biochem., 13(9), 10–13 (1978); Arthrobacter, Knecht, A. T., Jr., Thesis Dissertation, Louisiana State University, Order No. 621235 (1961); Beijerinckia, Laborde, A. L., and Gibson, D. T., "Metabolism of Dibenzothiophene by a Beijerinckia Species," Appl. Environ. Microbiol., 34, 783–790 (1977); Rhizobium, Malik, K. A., (supra); Pseudomonas, Hou, C. T. and Laskin, A. I., "Microbial Conversion of Dibenzothiophene," Dev. Ind. Microbiol., 17, 351–362 (1976); Isbister, J. D. and Kobylinski, E. A., "Microbial Desulfurization of Coal in Processing and Utilization of High Sulfur Coals," Coal Science and Technology Series, No. 9, 627, Attia, Y. A., Ed. Amsterdam: Elsevier (1985); Knecht, A. T., Jr., (supra); Kodama, K., Nakatani, S., Umehara, K., Shimizu, K., Minoda, Y., and Yamada, K., "Microbial Conversion of Petrosulfur Compounds: Isolation and Identification of Products from Dibenzothiophene," Agr. Biolog. Chem., 34, 1320–1324 (1970);. Monticello, D. J., Bakker, D., and Finnerty, W. R., "Plasmid Mediated Degradation of Dibenzothiophene by Pseudomonas Species," Appl Environ. Microbiol., 49, 756–760 (1985);. Sulfolobus, Kargi, F. and Robinson, J. M., "Microbial Oxidation of Dibenzothiophene by the Thermophilic Organisms *Sulfolobus acidocaldarius*," Biotech. and Bioeng., 126, 687–690 (1984). The pathway of microbial degradation of DBT in each of the above cases except in Isbister, et al., (supra), is by C—C bond cleavage according to microbial degradation pathways of DBT originally established by Kodama, et al., (supra). Microbial degradation of organic sulfur-containing carbonaceous materials by C—C bond cleavage results in the loss of a large portion of the calorific value of the carbonaceous fuel. According to the Kodama, et al. (supra), C—C bond cleavage microbial degradation of DBT, sulfur-containing end products are 3-hydroxybenzothiophene sulfoxide, 2-formyl benzothiophene, or benzothiophene. A recent article, published after filing of the parent patent application, teaches degradation of dibenzothiophene resulting in carbon destruction, van Afferden, M., Schacht, S., Klein, J. and Trupper, H. G., "Degradation of Dibenzothiophene by Brevibacterium sp.DO", Arch. of Microbiol., 153, 324–328 (1990).

It is more desirable to follow a microbial degradation route which removes sulfur from the molecule without removing carbon from the molecule, thereby retaining calorific value of the fuel to a greater degree than is possible by carbon degradative pathways. Such sulfur-specific metabolism of the organic substrates requires cleavage of carbon-sulfur bonds in the organic sulfur-containing molecule. In the case of sulfur specific metabolism of dibenzothiophene, the end products are 2-hydroxybiphenyl and biomass. This C—S cleavage pathway is believed to proceed according to dibenzothiophene→ dibenzothiophene sulfoxide→dibenzothiophene sulfone→dibenzothiophene sulfonate→2-hydroxybiphenyl. The monohydroxy product of this C—S cleavage route distinguishes it from routes leading to significant amounts of dihydroxybiphenyl.

The only prior microorganism known to the present inventor allegedly capable of degradation of DBT by C—S cleavage is a Pseudomonas species as described by Isbister, (supra), and Pseudomonas ATCC 39381, as set forth in U.S. Pat. No. 4,562,156. The ATCC 39381 culture on deposit does not possess the C—S cleavage trait and the depositors of the culture have stated that the culture on deposit cannot be replaced as such cultures having the C—S cleavage trait to their knowledge do not exist. (4th Department of Energy Preparation, Utilization and Environmental Control Contractors Conference, U.S. Dept. of Energy, Pittsburgh Energy Technology Center, Pittsburgh, Pa. 15236, U.S.A., 1988). Mixed cultures obtained through growth under sulfur limited conditions have been capable of selective removal of sulfur from DBT, Kilbane, John J., "Sulfur-Specific Microbial Metabolism of Organic Compounds," Bioprocessing of Coals Workshop, Tysons Corner, Va., Aug. 16–18, 1988. A very recent article, published after filing of the parent patent application, teaches dibenzothiophene (DBT) metabolism by Corynebacterium sp. Strain SY1 and projects pathways of DBT metabolism substantially the same as those set forth for C—S bond cleavage earlier by the applicant in the parent and other earlier patent applications and patents, Omori, T., Monna, L., Saiki, Y., and Kodama, T., "Desulfurization of Dibenzothiophene by Corynebacterium sp. Strain SY1" App. & Environ. Microbiol. 58, 3, 911–915, March (1992).

SUMMARY OF THE INVENTION

It is an object of this invention to provide a microbial extract, particularly those comprising membrane fragments exhibiting selective C—S bond cleavage, and a process for removal of organically bound sulfur from sulfur-containing organic carbonaceous materials by contact with such membrane fragments.

It is an object of this invention to provide a microorganism membrane associated enzyme or enzymes, particularly those comprising enzymes capable of selective C—S bond cleavage, and a process for removal of organically bound sulfur from sulfur-containing organic carbonaceous materials by contact with such enzymes.

It is another object of this invention to provide a microbial extract, particularly those comprising membrane fragments capable of selective C—S bond cleavage, and a process for selective sulfur removal from organic sulfur-containing fossil and fossil derived fuels by contact with such membrane fragments.

It is another object of this invention to provide a microorganism membrane associated enzyme or enzymes, particularly those capable of selective C—S bond cleavage, and a process for selective sulfur removal from organic sulfur-containing fossil and fossil derived fuels by contact with such enzymes.

It is yet another object of this invention to provide a microbial extract, particularly those comprising membrane fragments, and process capable of specific cleavage of C—S bonds in reactions of organic carbonaceous materials, such as in organic synthesis and in recycling operations, such as recycling of rubber products.

It is yet another object of this invention to provide a microorganism membrane associated enzyme or enzymes and process capable of specific cleavage of C—S bonds in reactions of organic carbonaceous materials, such as in organic synthesis and in recycling operations, such as recycling of rubber products.

It is still another object of this invention to provide a microbial extract, particularly those comprising membrane fragments, and/or membrane associated enzyme or enzymes capable of cleavage of organic C—S bonding and is stable and retains its sulfur specific characteristics under non-aqueous and broadened process conditions.

It is another object of this invention to provide a microbial extract, particularly those comprising membrane fragments, and/or membrane associated enzyme or enzymes and process for specific sulfur removal from dibenzothiophene resulting in the primary organic product of 2-hydroxybiphenyl under non-aqueous and broadened process conditions.

The above and other objects and advantages, as will become evident from reading of this description, may be achieved by an extract comprising membrane fragments and/or membrane associated enzyme or enzymes which have the ability of selective cleavage of organic C—S bonds.

Extracts of membrane fragments and/or membrane associated enzyme or enzymes having these properties from *Rhodococcus rhodochrous* and *Bacillus sphaericus* microorganisms and their derivatives are preferred. The above and other objects and advantages have been achieved by extracts comprising membrane fragments and/or membrane associated enzyme or enzymes from mutant microorganisms which have been produced and identified as *Rhodococcus rhodochrous* ATCC No. 53968 and *Bacillus sphaericus* ATCC No. 53969. The culture of each of these organisms has been deposited under the Budapest Treaty with American Type Culture Collection, 12301 Park Lawn Drive, Rockville, Md., U.S.A. 20852, and assigned the above ATCC Numbers. *Rhodococcus rhodochrous* ATCC No. 53968 is more fully described in U. S. Pat. No. 5,104,801 and *Bacillus sphaericus* ATCC No. 53969 is more fully described in U.S. Pat. No. 5,002,888, all commonly owned with this application.

*Rhodococcus rhodochrous* ATCC No. 53968 or *Bacillus sphaericus* ATCC No. 53969 may be prepared by inoculating a growth medium with mixed bacteria derived from sites having present materials of C—S bonding desired to be cleaved, the growth medium comprising mineral nutrients, an assimilable source of carbon, and in substantial absence of a sulfur-containing compound, except compounds having sulfur present only in C—S bonding of the type desired to be cleaved; growing the bacterial culture in the presence of oxygen at temperatures about 20° to about 34° C. and in the substantial absence of a sulfur-containing compound except compounds having sulfur present only in C—S bonding of the type desired to be cleaved for sufficient time to selectively produce *Rhodococcus rhodochrous* ATCC No. 53968 and/or *Bacillus sphaericus* ATCC No. 53969 which has the property of sulfur metabolism by selective cleavage of C—S bonds in organic carbonaceous materials. To produce *Bacillus sphaericus* ATCC No. 53969 a helper culture may be necessary to furnish nutrients necessary for *Bacillus sphaericus* ATCC No. 53969 growth. The helper culture provides nutrient requirements for the *Bacillus sphaericus* ATCC No. 53969, but has no ability to metabolize organic sulfur.

Extracts comprising membrane fragments may be prepared as a lysate from the above microorganisms by lysis processes. Any process providing a concentration of cell membrane fragments is suitable as long as chemicals responsible for the selective cleavage of C—S bonds are retained in the product. An enzyme or enzymes associated with membranes of the above microorganisms may be separated by enzyme extraction processes and are capable of cleavage of C—S bonds in organic carbonaceous materials. The enzyme or enzymes may be used in extracted form or may be further purified and used in purified form. As used throughout the description and claims, the terminology "enzyme" or "enzymes" is meant to include a single enzyme or a composition of enzymes in an extracted form or purified form. Use of these sulfur specific reactant agents of an extract comprising membrane fragments and/or an enzyme or enzymes associated with membranes having the capability of selective organic C—S bond cleavage permits use of selective organic sulfur removal processes using aqueous or non-aqueous media and temperatures in excess of those which a are required for microbial growth.

According to the present invention, a sulfur specific reactant agent selected from an extract comprising membrane fragments and/or an enzyme or enzymes associated with membranes and having selective C—S bond cleavage propeties may be mixed directly with organic sulfur containing organic carbonaceous liquids, such as oils, or may be mixed with organic liquids for contacting organic sulfur containing organic carbonaceous solids. As used throughout the description and claims, the terminology "contacting" is meant to include any means of promoting contact between the sulfur specific reactant agent and the sulfur containing organic compound, such as, through use of emulsions, microemulsions, immobilized extract/enzyme preparations, membrane reactors, agitation, sonication, and the like. Use of the sulfur specific reactant agent in an organic liquid avoids water/oil boundary barriers which exist when microorganism growth in an aqueous media is relied upon for organic sulfur removal. The sulfur specific reactant agent may be used in an aqueous medium if desired. Use of non-aqueous liquids is preferred since they may achieve higher catalytic rates, an expanded range of substrate utilization, and increased stability as compared to use of aqueous media. Higher organic sulfur removal rates may be achieved by operation of the sulfur removal process of this invention at temperatures higher than permitted when microorganism growth is relied upon for sulfur removal. Additionally, organic and inorganic sulfur may be liberated and removed in a single or continuous non-aqueous media process.

Sulfur content of sulfur-containing organic carbonaceous material may be reduced by contacting such sulfur containing organic carbonaceous material with a sulfur specific reactant agent derived from or associated with membranes of microorganisms, such as *Rhodococcus rhodochrous* and *Bacillus sphaericus* and their derivatives having the capability of selective organic C—S bond cleavage and most preferably *Rhodococcus rhodochrous* ATCC No. 53968 or *Bacillus sphaericus* ATCC No. 53969. The process is especially suitable for use where the sulfur-containing carbonaceous material is coal or hydrocarbon oil. Such processes can result in the removal of more than 80 percent, and preferably more than 90 percent, of the organically bound sulfur. The process for reducing the sulfur content of the sulfur-containing organic carbonaceous material occurs by cleavage of organic C—S bonds by a sulfur specific reactant derived from or associated with membranes having the capability of selective organic C—S bond cleavage, such as obtained from *Rhodococcus rhodochrous* and *Bacillus sphaericus* microorganisms having such properties, particularly from the microorganism *Rhodococcus rhodochrous* ATCC No. 53968 or *Bacillus sphaericus* ATCC No. 53969 and their derivatives. These sulfur specific reactants have the ability to selectively reduce the sulfur content of sulfur-containing organic carbonaceous material by cleavage of organic C—S bonds resulting, in the principal organic end product of monohydroxybiphenyl from dibenzothiophene. Extracts comprising membrane fragments and/or enzyme or enzymes associated with membranes of derivative microorganisms particularly of *Rhodococcus rhodochrous* ATCC No. 53968 and *Bacillus sphaericus* ATCC 53969 have been shown to exhibit the ability to selectively reduce the sulfur content of sulfur-containing organic carbonaceous material by cleavage of organic C—S bonds in the same fashion as described above and are considered to be included when the terminology "sulfur specific reactant" is used in this description and claims.

When it is desired to selectively reduce the sulfur content of organic carbonaceous materials having very small pore sizes, such as coal, it is preferred to use the sulfur specific reactant enzymes and membrane fragments since the smaller size of enzymes or membrane fragments as compared with intact bacterial cells can access pores not available to the bacteria and provide more effective contact of active materials, having the effect of increasing accessible surface area.

DESCRIPTION OF PREFERRED EMBODIMENTS

Environmental cultures having a known history of exposure to organosulfur compounds as well as enrichment cultures using as carbon sources acetate, benzene, benzoic acid, ethanol, glucose, glycerol, nutrient broth, succinate, and toluene and organic sulfur compounds benzothiophene, dibenzothiophene, thiophene, trithiane, produced bacterial cultures capable of metabolizing each of the organic sulfur compounds used. All of the environmental isolates and enrichment cultures tested were found to metabolize organosulfur compounds by initiating biodegradation at the carbon-carbon bond except for a mixed culture enriched with thiophene as its sole source of sulfur which was shown to be capable of carbon-sulfur bond cleavage for about 20% of its products, the remaining 80% being the result of carbon-carbon bond cleavage. The most successful microorganism for sulfur utilization from organosulfur compounds was Pseudomonas isolated from enrichment cultures employing DBT as the sole source of sulfur. This Pseudomonas species while capable of utilizing organically bound sulfur failed to show specificity for the oxidation of carbon-sulfur bonds. This shows the failure of enrichment culture development of a naturally occurring microorganism showing specificity for oxidation of organic C—S bonds. Thus, an unnatural, selective mutation process must be utilized to develop a microorganism having such selective sulfur metabolism.

Microorganisms having sulfur-specific metabolic abilities with respect to organic substrates were developed by selection through a continuous culture coal bioreactor/selectostat in which nutrients and organically bound sulfur not normally found in living tissue may be supplied in the substantial absence of other available sulfur such as sulfates, vitamins, amino acids and the like. The growth media should supply organic and inorganic nutrients for good microorganism growth, but be devoid of inorganic and organic sulfur-containing compounds except those organic sulfur-containing compounds desired to be metabolized by the mutant microorganism. A suitable media for growth of microorganisms under organosulfur conditions may suitably be a composition of mineral nutrients, such as 4 gms $K_2HPO_4$, 4 gms, $Na_2HPO_4$, 2 gms $NH_4Cl$, 0.2 gm $MgCl_2 \cdot 6H_2O$, 0.001 gm $CaCl_2 \cdot 2H_2O$, and 0.001 gm $FeCl_3 \cdot 6H_2O$ per liter of distilled, deionized water. Any assimilable carbon source devoid of sulfur may be used in amounts to support desired microbial growth. Suitable assimilable carbon sources include glucose, glycerol, sodium acetate, sodium benzoate, sodium succinate, and sucrose at concentrations of about 20 mM and benzene, ethanol, isobutanol, and toluene may be used as vapors in the head space of the bacterial growth bioreactors. Organosulfur compounds having organic C—S bonds are suitable, such as, benzothiophene, benzyldisulfide, dibenzothiophene, dibenzothiophene sulfone, phenyldisulfide, thianthrene, thioxanthene (Aldrich Chemical Company, Milwaukee, Wis.), dibenzothiophene sulfoxide (ICN Biomedicals, K&K Labs, Plainview, N.J.) and trithiane (Fairfield Chemical Company, P.O. Box 20, Clythewood, S.C.) may be used over concentration ranges which support microbial growth, in the order of about 20 mM and thiophene (Aldrich Chemical Company) may be used as a vapor, as well as numerous other compounds having organic C—S bonds. Nutrient broth (Difco Laboratories, Detroit, Mich.) or the above growth media solidified with about 15 g of agar (Difco) per liter may be employed for streaking or plating bacterial cultures. Bacterial growth may be monitored turbidimetrically using a Klett-Sommerson colorimeter or by enumerating colony forming units on appropriate agar.

Inoculum may be prepared by adding 5 gm samples of soil obtained from coal storage sites and from petroleum refinery sites to 10 ml of the above growth media, vortexed for 60 seconds, and allowed to settle for 30 minutes. The supernatants may be removed with a Pasteur pipette and used directly or diluted with an equal volume of nutrient broth and incubated at room temperature for about 24 to 48 hours before being used to inoculate the bioreactors.

Bioreactors/selectostats were of special design to provide continuous flow of liquid nutrients while retaining coal or organosulfur solids. The same batch of coal or organosulfur compound remains within the bioreactor for the duration of its operation whereas the aqueous phase media may be continuously supplied to the bioreactor. The retention of coal within the bioreactor for long periods of time may be accomplished by using relatively large particles of coal, typically −9 +12 mesh, and the use of an inclined, non-mixed sedimentation tube containing several weirs/baffles from which the bioreactor effluent may be withdrawn at relatively slow flow rates. The effluent withdrawal rates may be adjusted according to the ability of the microorganism to respond to the sulfur limitation challenge, typically, hydraulic retention times may be in the order of 72 hours.

The selectostats may be monitored frequently to determine suitable carbon source feed rate and to assay for presence of biologically available sulfur in the effluent. This may be achieved by centrifuging fresh bioreactor effluent to remove coal fines and particles of organosulfur substrate and bacteria followed by use of the supernatant in bacterial growth tests. Four cultures are prepared: the supernatant; the supernatant with 15 mM $SO_4$; a supernatant with 20 mM carbon source; and a supernatant with 15 mM $SO_4$ and 20 mM carbon source, each inoculated with a microbial culture at $10^5$ microorganism/ml and incubated for 2 to 5 days with shaking at growth temperatures for the microorganism being tested. Bacterial growth is monitored turbidimetrically or by determining colony-forming units. The carbon source sample serves to indicate the presence of biologically available sulfur in the effluent supernatant while the sample with added sulfate serves to indicate the presence of a carbon source in the effluent supernatant, and the sample containing both the carbon and added sulfate serves to indicate the presence of inhibitory substances in the effluent supernatant.

The ability of bacteria to utilize organic sulfur compounds for growth can be measured by the Sulfur Bioavailability Assay. This assay is based on the fact that all life requires some sulfur for growth and, therefore, a situation can be created whereby quantifying bacterial growth provides a measure of the utilization of any organic or inorganic compound as a source of sulfur. In practice, growth media containing a carbon source at 20 mM is used unamended, amended with 20 mM $Na_2SO_4$, and amended with 20 mM of an organosulfur compound or an inorganic sulfur compound. Each of the three conditions are then inoculated with a microbial culture at $10^5$ microorganisms/mL and incubated for 2 to 5 days with shaking at temperatures appropriate for the microorganism being tested. Bacterial growth is monitored turbidimetrically or by determining colony forming units. The unamended sample serves as a negative control while the sample amended with sulfate serves as a positive control, and both controls are used to assess whether bacterial growth occurred at the expense of sulfur obtained from the organosulfur test compound.

Development of the selective organic sulfur-specific culture may be accelerated by mutagenesis by exposure to 1-methyl-3-nitro-1-nitrosoguanidine (NTG) or to ultraviolet irradiation. Mutagenesis with NTG may be performed by spreading a solution of bacteria on an agar plate and placing a crystal of NTG in the center of the plate. During incubation, the NTG crystal dissolves in the agar forming a diffusional concentration gradient which results in no bacterial growth at the center and healthy growth at the outer perimeter of the plate. Between these extremes, a narrow zone of intermediate growth is readily observable and mutagenized bacteria are obtained from this zone. Bacteria for UV-mutagenesis may be pelleted from liquid culture by centrifugation, washed with the above growth media, and resuspended in a volume of the above growth media. Three milliliter portions may be placed in uncovered sterile petri dishes and exposed to doses of UV irradiation sufficient to cause 2 logs of killing, typically 10 J/m$^2$.

A mixed bacterial culture obtained from the selectostats after several months operation was shown to be capable of utilizing a range of organosulfur compounds as the sole source of sulfur as determined by the Sulfur Bioavailability Assay described above. Specific C—S bond cleavage in dibenzothiophene by this mixed culture was demonstrated by gas chromatographic/mass spectrometric analysis. Standard microbiological techniques were used to obtain pure cultures representative of each bacterial type present in the mixed culture. Each pure culture was individually tested for its ability to utilize organosulfur compounds as the sole source of sulfur by the Sulfur Bioavailability Assay. Isolated cultures which exhibited the ability to utilize organosulfur compounds as the sole source of sulfur have been identified as *Rhodococcus rhodochrous* and *Bacillus sphaericus*. The *Rhodococcus rhodochrous* strain has been deposited with American Type Culture Collection and assigned number ATCC 53968. The strain is characterized by gram positive short rods of about 0.5μ length, producing peach-colored colonies on nutrient agar and having high organic sulfur specificity by cleavage of C—S bonding. The *Bacillus sphaericus* strain has been deposited with American Type Culture Collection and assigned number ATCC 53969. The strain is characterized by gram positive short rods of about 0.5μ length, producing beige/white-colored colonies on nutrient agar and having high organic sulfur specificity by cleavage of C—S bonding.

*Bacillus sphaericus* ATCC No. 53969 does not grow in chemically defined mineral salts medium in the presence of assimilable carbon and an organosulfur compound having sulfur present only in C—S bonding without the presence of a nutritional helper culture providing cross-feeding necessary for growth. Any bacteria providing nutrients for growth under such conditions are satisfactory. Suitable nutritional helper cultures providing completion of elements of nutrition for growth of *Bacillus sphaericus* ATCC No. 53969 may be readily ascertained by one skilled in the art. Presently known suitable helper cultures include several Enterobacter species, such as *E. aerogenes, E. agglomerans*, and *E. cloacae*, and a Klebsiella species. The helper culture has no ability to specifically desulfurize organic sulfur compounds.

To confirm the species identity, membrane lipids of the *Rhodococcus rhodochrous* ATCC 53968 were solvent extracted, derivatized and analyzed by gas chromatography. The chromatogram was compared with lipid analyses of known Rhodococcus cultures recorded in a computer library supplied by Microcheck, Inc. (Northfield, Vt.). These tests identify ATCC 53968 as *Rhodococcus rhodochrous* as shown by Table 1 showing all fatty acids found in the extract compared with the library entry listed in elution order in the left column. An "x" is printed for each acid on the line opposite the fatty acid name indicating the amount of that acid and the library entry mean value for the acid identified with a "+". In cases where the library mean percentage and the actual percentage in the extract are the same an "*" is printed. A dashed line gives a +2 or −2 standard deviation window around the mean value for the library entry. Examination of Table 1 shows high certainty in the identification of the *Rhodococcus rhodochrous*.

TABLE 1

Membrane Lipid Analysis of *Rhodococcus rhodochrous* ATCC No. 53968

| Lipid Type | Percentage (0 — 5 — 10 — 15 — 20 — 25 — 30 — 35 — 40 — 45 — 50) |
|---|---|
| 14:0 | — — + x — — |
| 15:0 | — — * — — — — |
| 16:1 B | * — — |
| 16:1 CIS 9 | — — x + — — — — |
| 16:0 | — — — — — + — — x — — |
| 17:1 ISO 6 | * — — |
| 17:1 B | — — — + x — — |
| unknown 16.918 | * — — |
| 17:0 | — — * — — |
| 18:1 ISO F | — * — — |
| 18:1 CIS 9 | — — — — — x — — — — + — — — — — — — — — |
| 18:0 | — — x + — — |
| 10 Me 18:0 | — — — — — — — — * — — — — — — — |
| 19:0 | + — — x |
| 20:0 | — + x — — |
| SUMMED FEATURE 4 | — — x — — — + — — — — — — — |
| SUMMED FEATURE 8 | — * — — — |

To confirm the species identity, membrane lipids of the *Bacillus sphaericus* ATCC 53969 were solvent extracted, derivatized and analyzed by gas chromatography in the same manner. The chromatogram was compared with lipid analyses of known Bacillus cultures recorded in a computer library supplied by Microcheck, Inc. (Northfield, Vt.). These tests identify ATCC 53969 as *Bacillus sphaericus* as shown by Table 2. Examination of Table 2 shows high certainty in the identification of the *Bacillus sphaericus*.

TABLE 2

Membrane Lipid Analysis of
Bacillus sphaericus ATCC No. 53969

| Lipid Type | Percentage |
| --- | --- |
| | 0   5   10   15   20   25   30   35   40   45   50   55   60   65 |
| 14:0 ISO | - - x + - - - |
| 14:0 | + - x |
| 15:0 ISO |                                  - - - - - - - - - - - - - - - - - - - - + - - - - - - - - - - - - - - - - x - |
| 15:0 ANTEISO | - - - x + - - - |
| 15:0 | x + - |
| 16:1 ISO E |         x - - - - + - - - |
| 16:0 ISO |     x - - - - - - - - - + - - - - - - - - - - |
| 16:1 A | - - + x - |
| 16:0 | - + x |
| 17:1 ISO E | - + - x |
| 17:0 ISO | - - x - + - - - - |
| 17:0 ANTEISO | - x - + - - - |
| SUMMED FEATURE 5 | - + x - |

Rhodococcus ATCC 53968 was compared with other Rhodococcus species obtained from American Type Culture Collection with respect to carbon sources which would support the growth of these cultures. The cultures were streaked onto the specified agar plates containing the indicated carbon sources and/or inoculated into liquid medium and evaluated after incubating the cultures for 96 hours at 30° C. The results of carbon source utilization studies using a variety of Rhodococcus strains are shown in Table 3. It appears entirely consistent from carbon sources which support the growth of the microorganism that *Rhodococcus rhodochrous* ATCC 53968 is in fact *Rhodococcus rhodochrous*.

Each of the Rhodococcus species listed in Table 3 were evaluated using the above described sulfur bioavailability assay to determine their ability to utilize organically bound sulfur in DBT. Most strains were tested several times using a variety of substrates. The ATCC 53968 strain was the only Rhodococcus species tested having the C—S bond cleavage property. Additional tests with *Rhodococcus rhodochrous* ATCC 53968 have shown that trithiane, thianthrene, dibenzothiophene sulfoxide and dibenzothiophene sulfone and other organosulfur compounds may also be used as sulfur sources for *Rhodococcus rhodochrous* ATCC 53968.

The *Rhodococcus rhodochrous* ATCC 53968 strain has shown a doubling time in the presence of either dibenzothiophene or inorganic sulfate to be about 12 hours. The growth rate of *Rhodococcus rhodochrous* ATCC 53968 is much faster on rich medium (Luria Broth), however, other microorganisms exhibit even faster growth rates on the chemically defined and the rich medium.

*Bacillus sphaericus* ATCC 53969 was compared in the same manner as described above with other Bacillus species obtained from American Type Culture Collection with respect to carbon sources which would support the growth of these cultures. The results of carbon source utilization studies using a variety of Bacillus strains are shown in Table 4. Carbon source utilization data obtained with *Bacillus sphaericus* ATCC 53969 is identical to that obtained with *Bacillus sphaericus* ATCC 14577. However, a chemically defined growth medium has not been found in which *Bacillus sphaericus* ATCC 53969 will grow as a pure culture. Additional microbiological tests, including growth on nutrient agar, microscopic observation and growth temperature studies yield identical results with both *B. sphaericus* 14577 and *B. sphaericus* 53969. These data, in conjunction with membrane lipid analysis data, indicate that the microorganism ATCC 53969 is a *Bacillus sphaericus* microorganism.

The Bacillus species listed in Table 4 were evaluated using the above described sulfur bioavailability assay to determine their ability to utilize organically bound sulfur in DBT. Most strains were tested several times using a variety of substrates. The ATCC 53969 strain was the only Bacillus species tested having the C—S bond cleavage property. *Bacillus sphaericus* ATCC No. 53969 was grown in the presence of *Enterobacter aerogenes* or *Enterobacter agglomerans* as a nutrient helper culture. This desulfurization trait in *Bacillus sphaericus* ATCC 53969 has been observed to be stable throughout numerous subculturing events on both selective and non-selective medium.

The *Bacillus sphaericus* ATCC 53969 when grown with a helper culture in chemically defined mineral salts medium, with DBT serving as the sole source of sulfur, results in approximately 0.2 mM 2-hydroxybiphenyl detected in the medium. 2-hydroxybiphenyl is the only metabolite of DBT that has been detected under these conditions.

The stability of the desulfurization trait of *Rhodococcus rhodochrous* ATCC 53968 has been evaluated by growing the culture under non-selective conditions for multiple generations and more than 200 single colonies were obtained and tested by the above described sulfur bioavailability assay, all cultures proving to be competent for desulfurization by C—S bond cleavage. It appears that under the above culture conditions, the C—S bond cleavage ability possessed by the *Rhodococcus rhodochrous* ATCC 53968 is a stable trait. The desulfurization trait of *Rhodococcus rhodochrous* ATCC 53968 is maintained through heat shocking. Growth of *Rhodococcus rhodochrous* ATCC 53968 is severely retarded or absent at 37° and 42° C. when incubated at those temperatures for 48 hours. Seventy-two single colonies of

TABLE 3

| Rhodococcus strains | ATCC # | Glycerol | Sucrose | Citrate | Benzoate | Acetate | Glucose | Ethanol | Succinate | Isobutanol |
|---|---|---|---|---|---|---|---|---|---|---|
| R. rhodochrous | 53968 | ++ | +/− | − | ++ | + | + | + | − | + |
| R. rhodochrous | 13808 | +/− | +/− | − | ++ | + | + | + | + | +++ |
| R. rhodochrous | 19149 | − | + | + | ++ | + | +++ | +++ | + | +++ |
| R. rhodochrous | 19067 | − | + | − | ++ | + | + | +++ | + | +++ |
| R. erythropolis | 19369 | +/− | − | +/− | − | + | ++ | +++ | + | +++ |
| R. erythropolis | 4277 | − | − | − | +/− | + | + | ++ | + | ++ |
| R. globerulus | 19370 | + | + | +/− | ++ | + | + | ++ | + | ++ |
| R. globerulus | 15903 | +++ | + | − | ++ | + | ++ | +++ | + | +++ |
| R. equi | 14887 | − | +/− | − | +/− | − | + | − | − | − |

TABLE 4

| Bacillus strains | ATCC # | Glycerol | Sucrose | Citrate | Benzoate | Acetate | Glucose | Ethanol | Succinate | Isobutanol |
|---|---|---|---|---|---|---|---|---|---|---|
| B. subtilis | 33608 | − | − | − | − | − | + | − | − | − |
| B. sphaericus | 14577 | − | − | − | − | − | − | − | − | − |
| B. sphaericus | 53969 | − | − | − | − | − | − | − | − | − | desulfurization competent *Rhodococcus rhodochrous* ATCC 53968 have been streaked onto nutrient agar, incubated at 37° C. or 42° C. for 48 hours followed by incubation at 30° C. for 72 hours and tested by the above described sulfur bioavailability assay, with all colonies exhibiting stable maintenance of the desulfurization trait.

The mutant culture *Rhodococcus rhodochrous* ATCC 53968 was inoculated into a mineral salts glucose bacterial growth medium containing dibenzothiophene as the sole sulfur source. After growth at 30° C. for 72 hours, the cultures were centrifuged, the supernatants processed by solid-phase extraction using C-18 silica compounds, eluted with dichloromethane, and analyzed using gas chromatography/mass spectrometry to identify and quantify the metabolites of dibenzothiophene. The results are shown in Table 5, quantitation of the metabolites being accomplished by spiking the dichloromethane eluates with a known concentration of ethylnapthalene and comparing metabolite peaks with retention times and concentration curves prepared with pure chemical compounds. Compounds that were specifically looked for are listed in Table 5. The fact that only 2-hydroxybiphenyl was found and that 3-hydroxy-2-formyl-benzothiophene and any other compounds known to be formed in the carbon destructive pathway of DBT degradation were not found demonstrates that the *Rhodococcus rhodochrous* ATCC 53968 metabolizes dibenzothiophene via C—S bond cleavage route and not by a C—C bond cleavage route as do the microorganisms of the prior art.

TABLE 5

METABOLITES OF *RHODOCOCCUS RHODOCHROUS* ATCC 53968

| Compound | | Mol. Wt. | ppm |
|---|---|---|---|
| * | Dibenzothiophene-5-oxide | 200 | BDL |
|  | plus Phenoxathiin | 200 |  |
| ** | Dihydroxybiphenyl | 186 | BDL |
| ** | 2-hydroxybiphenyl | 170 | 35.27 |
| + | 3-hydroxy-2-formyl-benzothiophene | 178 | BDL |
| ** | Biphenyl | 154 | BDL |
| + | Benzothiophene | 134 | BDL |
| + | Three isomers of $C_8H_6OS$: (hydroxybenzothiophene) |  |  |
|  | No. 1 | 150 | BDL |
|  | No. 2 | 150 | BDL |
|  | No. 3 | 150 | BDL |
| + | $C_9H_8OS$ | 164 | BDL |
| + | $C_9H_8O_2S$ | 180 | BDL |
| + | $C_9H_6OS$ | 162 | BDL |
| + | $C_{10}H_{10}OS$ or $C_9H_6O_2S$ | 178 | BDL |
| + | $C_8H_8O_2S$ isomers a) | 168 | BDL |
|  | b) | 168 | BDL |
| + | Formula (?) | 220 | BDL |

* C-S cleavage intermediate
** C-S cleavage product
+ C-C cleavage product
BDL means below detection level of ~ 0.001

*Rhodococcus rhodochrous* ATCC 53968 derivatives have been shown to retain the same or better selective desulfurization trait of the *Rhodococcus rhodochrous* ATCC 53968 strain. Derivative microorganisms of *Rhodococcus rhodochrous* ATCC 53968 have been obtained which have additionally exhibited resistance to the antibiotics ampicillin, cephalordine, naladixic acid, spectinomycin, streptomycin, rifampicin, and combinations of two or three of these resistance traits. These antibiotic resistant derivatives are the result of genetic mutations, although not the product of recombinant DNA techniques. Other derivative microorganisms of *Rhodococcus rhodochrous* ATCC 53968 have been demonstrated to be auxotrophic mutants/derivatives defective in the ability to synthesize one or more essential amino acid or vitamin. Some of the auxotrophic mutant derivatives have been exhibited to be defective in their ability to synthesize sulfur-containing amino acids cysteine and methionine. All of the *Rhodococcus rhodochrous* ATCC 53968 derivative microorganisms exhibiting antibiotic resistance and auxotrophic properties have retained their ability to cleave organic C—S bonds.

I have found tolyldisulfide to specifically inhibit the organic C—S bond cleavage trait of *Rhodococcus rhodochrous* ATCC 53968 when present with another organic sulfur-containing compound, such as dibenzothiophene. However, tolyldisulfide is not generally inhibitory to *Rhodococcus rhodochrous* ATCC 53968 since it does not inhibit utilization of inorganic sulfate for growth. Mutants/derivatives of *Rhodococcus rhodochrous* ATCC 53968 have been selected which overcome such inhibition of the organic C—S bond cleavage trait and were able to grow with tolyldisulfide as their sole source of sulfur. Such derivatives have exhibited about a 25 percent enhancement in their ability to metabolize dibenzothiophene by organic C—S bond cleavage.

Another derivative culture of *Rhodococcus rhodochrous* ATCC 53968 has been isolated which exhibits the organic C—S bond cleavage trait in the presence of high levels, in the order of about 20 mM, of inorganic sulfate. The microorganism *Rhodococcus rhodochrous* ATCC 53968 itself exhibits reduction in the organic C—S bond cleavage trait in such concentrations of inorganic sulfate.

An antibiotic resistant derivative of *Rhodococcus rhodochrous* ATCC 53968 was used in mixed culture with *Enterobacter aerogenes*. The mixed inoculum contained a tenfold excess of *Rhodococcus rhodochrous* ATCC 53968 relative to *E. aerogenes* and growth was monitored in the above defined growth medium, glycerol, and DBT as the sole source of sulfur. At 50, 70, 140 and 240 hours samples of the culture were used to prepare dilution series which were plated onto nutrient agar and nutrient agar containing 250 micrograms/mL streptomycin. *E. aerogenes* grew faster than the *Rhodococcus rhodochrous* ATCC 53968 derivative on the nutrient agar while only the *Rhodococcus rhodochrous* ATCC 53968 derivative grew on nutrient agar containing antibiotic. The *Rhodococcus rhodochrous* ATCC 53968 derivative grew rapidly during the first 70–80 hours since it is the only organism capable of metabolizing sulfur from DBT. However, after about 50–60 hours, even though *E. aerogenes* cannot metabolize DBT, it begins rapid growth and at 240 hours is present in nearly three orders of magnitude greater abundance than the *Rhodococcus rhodochrous* ATCC 53968 derivative. This suggests that DBT is metabolized in association with the outer cell membrane of the *Rhodococcus rhodochrous* ATCC 53968 bacteria in a manner such that sulfur liberated from DBT by *Rhodococcus rhodochrous* ATCC 53968 is available for metabolism by other bacteria.

*Bacillus sphaericus* ATCC 53969 derivatives retain the same or better selective desulfurization trait of the ATCC 53969 strain. *Bacillus sphaericus* ATCC 53969 derivatives having the same selective desulfurization trait are suitable for use in any of the described desulfurization processes and are intended to be included for such uses.

The desulfurization trait of *Bacillus sphaericus* ATCC 53969 is apparently associated with the outer cell membrane of this microorganism. This fact is supported by the observation that the helper culture, as a pure culture, has no ability to grow in chemically defined mineral salts medium in which DBT serves as the sole sulfur source. However, when a desulfurization competent microorganism, specifically *Bacillus sphaericus* ATCC 53969, is simultaneously present, this helper culture grows profusely. This profuse growth of the helper culture could only occur if sulfur liberated from DBT by *Bacillus sphaericus* ATCC 53969 was made available for use by the helper culture.

*Rhodococcus rhodochrous* ATCC No. 53968 derivatives and *Bacillus sphaericus* ATCC No. 53969 derivatives resistant to 500 micrograms/ml of streptomycin were each mixed with *Enterobacter agglomerans*. The *Enterobacter agglomerans* culture was sensitive to streptomycin, was unable to grow under sulfur bioavailability assay conditions, and was unable to convert dibenzothiophene to detectable quantities of 2-hydroxybiphenyl. Pure cultures and mixed cultures were plated onto nutrient agar with and without an amount of streptomycin which would kill the Enterobacter but not affect the Rhodococcus or the Bacillus. After 40 hours, the density of Rhodococcus in the pure cell culture was $2.6 \times 10^6$ cells/ml and in the mixed culture was $2.4 \times 10^4$ cells/ml. After 360 hours, the Rhodococcus pure culture cell density was $3.5 \times 10^8$ to $2.2 \times 10^9$ cells/ml; Rhodococcus in the mixed Rhodococcus/Enterobacter culture was $2.7 \times 10^6$ cells/ml with the number of total cells being $5.5 \times 10^8$ cells/ml; Bacillus in the mixed Bacillus/Enterobacter culture was $6.8 \times 10^5$ cells/ml with the number of total cells being $3.2 \times 10^8$ cells/ml. Even though these mixed cultures contained manyfold fewer cells capable of C—S bond cleavage in metabolism of dibenzothiophene, $2.7 \times 10^6/5.5 \times 10^8$ for Rhodococcus and $6.8 \times 10^5/3.2 \times 10^8$ for Bacillus, they were, after about 300 hours, capable of producing nearly identical end quantities of 2-hydroxybiphenyl as compared to the pure cultures of Rhodococcus. It is clear from these growth studies that growth of the *Enterobacter agglomerans* in the mixed cultures was due to sulfur having been made available by the Rhodococcus or Bacillus metabolism of dibenzothiozene indicating that the C—S bond cleavage probably occurs at the exterior surface of the microorganisms and is associated with the cell walls. This conclusion seems warranted because if the DBT was first taken into the Rhodococcus or Bacillus cells and sulfur subsequently liberated from the DBT in the cytoplasm, it is unlikely that sulfur would then be excreted from the Rhodococcus or Bacillus cells and made available to the Enterobacter cells.

*Rhodococcus rhodochrous* ATCC No. 53968 and *Enterobacter agglomerans* cultures were placed in growth cultures separated by a dialysis membrane and when dibenzothiophene was used as the sole sulfur source for growth, it has been shown that cell contact between Rhodococcus and Enterobacter cells is required for utilization by Enterobacter of sulfur liberated from dibenzothiophene metabolized by Rhodococcus. This is consistent with findings that culture supernatants of Rhodococcus grown with dibenzothiophene do not contain detectable levels of any sulfur containing compound other than dibenzothiophene. This again, is evidence of the C—S bond cleavage reaction taking place in conjunction with the outer membrane of the Rhodococcus microorganisms.

The sulfur content of sulfur-containing organic carbonaceous materials may be selectively reduced by contacting with a sulfur specific reactant agent. The sulfur specific reactant agent according to this invention may be an extract comprising membrane fragments and/or an enzyme or composition of enzymes associated with a cell membrane wherein the cell membrane has the ability of selective cleavage of organic C—S bonds. *Rhodococcus rhodochrous* and *Bacillus sphaericus* microorganisms having the ability of selective cleavage of organic C—S bonds are suitable sources for extracts comprising cell membrane fragments and/or an enzyme or enzymes associated with the cell membrane and particularly preferred sulfur specific reactant agents are from microorganisms *Rhodococcus rhodochrous* strain ATCC No. 53968 and/or *Bacillus sphaericus* strain ATCC No. 53969. These sulfur specific reactant agents may be used in aqueous or non-aqueous media for the highly efficient removal of organic sulfur from organic sulfur-containing carbonaceous materials, particularly naturally occurring fossil fuels such as coal, petroleum, shale, oil, lignite, and synthetic fuels derived therefrom. Contacting of the sulfur-containing organic carbonaceous material may be effected by any means known to the art, such as by emulsions, fixed bed reactors, counter-flow reactors and other means of high surface area contacting.

Suitable non-aqueous media include organic liquids, such as, kerosene, crude oils, petroleum distillates, vegetable oils, and other light oils, glycerol, dimethylformamide, methanol, ethanol, benzene, toluene, octanol, octane, ethyl acetate, and hexane. Preferred organic liquids include kerosene, light oils, and methanol.

Extracts comprising membrane fragments may be prepared as a lysate from the above microorganisms by lysis processes, such as sonication, use of detergents, or use of a French press, as well known in the art. Any process providing a concentration of cell membrane fragments is suitable as long as the biochemical activity responsible for the selective cleavage of C—S bonds is available in the product.

Cell membrane preparation by lysis may be carried out by a large number of methods and the C—S bond cleavage property retained by the lysate. For example, I have obtained 50-fold decrease in cell viability in *Rhodococcus rhodochrous* ATCC No. 53968 lysed by French press followed by sonication with decrease in C—S bond cleavage activity only to one third of the original value, while French press treatment alone resulted in destruction of about 63% of the cells and retention of about 92% of the C—S bond cleavage activity. No C—S bond cleavage activity was found in any of the supernatants. These data make it clear that cell membrane extracts are effective for C—S bond cleavage activity. However, I have found the *Rhodococcus rhodochrous* ATCC No. 53968 microorganisms to be more difficult to lyse than *E. coli* and *B. subtilis*.

Enzymes associated with membranes of the above microorganisms may be separated by enzyme extraction processes and are capable of cleavage of C—S bonds in organic carbonaceous materials. Suitable enzyme extraction processes include lysis by sonication, detergents or by a French press followed by ammonium sulfate precipitation, fractionation, gel permeation chromatography, electrophoresis, isoelectric focusing, high pressure liquid chromatography, liquid chromatography, affinity chromatography, immunoprecipitation, or other suitable procedures, as well known in the art. The enzyme or enzymes may be used in extracted form or may be further purified and used in purified form.

Use of extracts comprising membrane fragments and/or enzymes associated with membranes of the specified microorganisms permits use of selective organic sulfur removal processes using non-aqueous or aqueous media and temperatures in excess of those which required for microbial growth. The organic sulfur is preferably selectively removed from organic sulfur-containing carbonaceous materials by contacting with the sulfur specific reactant agent in an organic medium for increased contact compatibility for a time sufficient to remove a substantial portion of the organic sulfur. According to the present invention, the sulfur specific reactant agent may be mixed directly with organic sulfur containing organic carbonaceous liquids, such as oils and may contain an emulsifying agent to promote emulsification, or may be mixed with organic liquids for contacting organic sulfur containing organic carbonaceous solids. The sulfur specific reactant agent should be used in an amount sufficient to provide a concentration effective to selectively react with a substantial portion of the organic sulfur within the time limitations of the process, both of which can be readily ascertained for specified reactant agents by one skilled in the art. Use of the sulfur specific reactant agent according to this invention in organic liquid media avoids water/oil boundary barriers which exist when microorganism growth and/or use of microorganisms or their products in an aqueous media is relied upon for organic sulfur removal. The sulfur specific reactant agent may be used in an aqueous medium if desired. Use of non-aqueous liquids is preferred since they achieve higher catalytic rates, an expanded range of substrate utilization, and increased stability as compared to use of aqueous media. Higher organic sulfur removal rates may be achieved by operation of the sulfur removal process at temperatures higher than permitted when microorganism growth is relied upon for sulfur removal. Sulfur removal reaction rates may be increased at temperatures greater than about 35° C., about 35° to about 100° C. being preferred. Additionally, organic and inorganic sulfur may be removed in a single or continuous non-aqueous media process. Any manners of contacting, as known to the art to result in highly efficient chemical reaction may be used, for example, ground coal may be agitated in an oil based liquid medium of extract comprising membrane fragments from *Rhodococcus rhodochrous* ATCC No. 53968 at a temperature in excess of that which limits culture growth for a time sufficient to obtain removal of more than about 80 percent of the organic sulfur.

Sulfur content of sulfur-containing organic carbonaceous material may be reduced by contacting such sulfur containing organic carbonaceous material with the sulfur specific reactant agent according to this invention. The process is especially suitable for use where the sulfur-containing carbonaceous material is coal or hydrocarbon oil. Such processes can result in the removal of more than 80 percent, and preferably more than 90 percent, of the organically bound sulfur.

The selective sulfur reactant agents according to this invention uniquely react with sulfur by cleavage of the C—S bonding in organic carbonaceous materials; for example, in reaction with dibenzothiophene, the organic end product is 2-hydroxybiphenyl. These properties render the selective sulfur reactant agents of this invention specific agents for cleavage of organic C—S bonding for destruction or synthesis of organosulfur compounds, such as, in organic process synthesis systems, herbicides, insecticides, defensins, and the like, and for uses in diagnostics, detection, and quantification, such as, in enzyme electrodes and immunological testing. Likewise, the selective sulfur reactant agents of this invention may be utilized in desulfurizing degradation of a wide variety of organic materials by cleavage of organic C—S bonding in recycling operations, such as in breakdown of sulfur containing organic molecules in rubber products.

The process of this invention results in the conversion of organic sulfur to sulfur in forms which may be separated and easily removed by a wide variety of methods readily apparent to one of ordinary skill in the art.

Biological membranes are generally hydrophobic and therefore extracts comprising membrane fragments and enzymes associated with membranes can naturally prefer non-aqueous systems. Extracts comprising membrane fragments and enzymes associated with membranes of the sulfur selective microorganisms *Rhodococcus rhodochrous* strain ATCC No. 53968 and *Bacillus sphaericus* strain ATCC No. 53969 according to the present invention can offer improved performance and process flexibility, such as the potential for simultaneous removal of both organic and inorganic sulfur from carbonaceous materials. Catalytic rates can be increased as much as several hundredfold, the range of substrates acted upon can be expanded, and tolerance to pH, temperature, and other environmental stresses can be dramatically improved by use of membrane fragments and enzymes in organic liquids. For example: the activity of peroxidase catalyzed pyrogallol oxidation is increased one hundredfold using reversed micelles of the enzyme in octanol versus its activity in water, Martinek, K., Levashov, A. V., Klyachko, N., Khmelnitski, Y. L., and Berezin, I. V., "Micellar Enzymology", *J. Biochem.*, 155, 453–468 (1986); the use of enzymes in non-aqueous or low-aqueous systems is reviewed in Khmelnitsky, Y. L., Levashov, A. V., Klyachko, N. L., and Martinek, K., "Engineering Biocatalytic Systems in Organic Media with Low Water Content," *Enzyme Micro. Technol.*, 10 (December, 1988); and biological reactions in treatment of coal using reverse micelle solutions showed cell-free enzyme extracts of *T. ferrooxidans* cells outperformed the whole-cell preparations, Lee, K. I. and Yen, T. F., "Coal Desulfurization Through Reverse Micelle Biocatalysis Process," ACS Div. of Fuel Chemistry, Int'l. Symposium, Los Angeles, Sep. 25–30, 1988.

The process of this invention may be advantageously used in conjunction with other processes to provide integrated processes, such as: removal of both inorganic and organic sulfur; and use of a chemical and/or physical process to expand the pore structure of coal to provide greater active surface area for more effective sulfur removal.

The sulfur specific reactant agents according to this invention may be prepared and stored for future use by freeze-drying and freezing with no loss of C—S bond cleavage ability. *Rhodococcus rhodochrous* ATCC No. 53968 cells were freeze-dried and immediately after freeze-drying were found to have, within experimental error, the same C—S bond cleavage activity as before freeze-drying. The freeze-dried cells were maintained in a screw capped bottle wrapped with aluminum foil for two and a half weeks at room temperature and exhibited a loss of about 23% of their original C—S bond activity. Similar cells were flash-frozen in liquid nitrogen and freeze-dried following which they were stored at room temperature for 24 hours and then found to maintain the C—S bond cleavage property essentially unchanged from prior to being flash-frozen and freeze-dried. Similar cells with 10% glycerol were frozen by placing them into a freezer at −70° C. without prior flash-freezing. After overnight and 7 days storage at −70° C. the cells exhibited their original C—S bond cleavage ability and after 8 weeks storage at −70° C. the cells exhibited about 91.5 of their original C—S bond cleavage activity. This work demonstrates that the biocatalysts of this invention can be prepared at one location, freeze-dried, and shipped at ambient temperature and much reduced weight and volume to desired used locations.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

I claim:

1. At least one enzyme obtainable from cell membranes of a microorganism selected from the group consisting of *Rhodococcus rhodochrous* strain ATCC No. 53968, *Bacillus sphaericus* strain ATCC No. 53969, and mutants thereof, said at least one enzyme having the ability to selectively react with organic sulfur of sulfur-containing organic carbonaceous material by cleavage of organic C—S bonds.

2. The at least one enzyme according to claim 1 wherein said microorganism is *Rhodococcus rhodochrous* strain ATCC No. 53968 or mutants thereof.

3. The at least one enzyme according to claim 1 wherein said microorganism is *Bacillus sphaericus* strain ATCC No. 53969 or mutants thereof.

* * * * *